United States Patent [19]

Markley et al.

[11] Patent Number: 4,474,602

[45] Date of Patent: Oct. 2, 1984

[54] SUBSTITUTED PYRIDYL COMPOUNDS, HERBICIDAL COMPOSITIONS AND METHOD OF USE

[75] Inventors: Lowell D. Markley; John M. Soper, both of Midland, Mich.

[73] Assignee: The Dow Chemical Company, Midland, Mich.

[21] Appl. No.: 340,608

[22] Filed: Jan. 19, 1982

Related U.S. Application Data

[63] Continuation of Ser. No. 218,244, Dec. 19, 1980, abandoned, which is a continuation-in-part of Ser. No. 97,262, Nov. 26, 1979, abandoned.

[51] Int. Cl.$^3$ .................. A01N 43/40; C07D 405/04; C07D 213/26
[52] U.S. Cl. ...................................... 71/94; 546/268; 546/296; 546/297; 546/302; 546/304; 546/307; 546/312; 546/339; 546/345; 546/346
[58] Field of Search .................. 71/94; 546/268, 345, 546/346, 296, 297, 302, 304, 307, 312, 339

[56] References Cited

U.S. PATENT DOCUMENTS

| | | | |
|---|---|---|---|
| 3,655,359 | 4/1972 | Krumkalns et al. | 71/94 |
| 3,930,835 | 1/1976 | Ozretich | 71/88 |
| 4,043,790 | 8/1977 | Krumkalns | 71/94 X |
| 4,105,435 | 8/1978 | Nishiyama et al. | 71/94 |
| 4,184,041 | 1/1980 | Nishiyama et al. | 546/345 |
| 4,260,766 | 4/1981 | Morris | 546/345 X |

*Primary Examiner*—Catherine L. Mills
*Attorney, Agent, or Firm*—Merlin B. Davey

[57] ABSTRACT

Substituted pyridyl compounds, e.g. 2,6-dichloro-4(2-(2,2,2-trichloroethyl)oxiranyl) pyridine; herbicidal compositions containing such compounds and method for the control of undesired vegetation using these compositions.

51 Claims, No Drawings

SUBSTITUTED PYRIDYL COMPOUNDS, HERBICIDAL COMPOSITIONS AND METHOD OF USE

CROSS-REFERENCE TO RELATED APPLICATIONS

This application is a continuation of Ser. No. 218,244 filed Dec. 19, 1980, now abandoned, which is a continuation-in-part of Ser. No. 097,262, filed Nov. 26, 1979, now abandoned.

BACKGROUND OF THE INVENTION

The control or elimination of undesired vegetation, particularly in the presence of desirable plant species, has long been a desideratum of the agricultural arts. Numerous methods and means for chemically controlling or eliminating undesired plants have been proposed such as those described, for example, in U.S. Pat. Nos. 4,018,801; 3,719,465; 3,183,074; 3,324,147; 3,509,222; 3,373,011 and 4,211,549.

Notwithstanding the progress that has been made in the chemical control of undesired vegetation there is still a need for herbicides which are more cost effective and selective.

SUMMARY OF THE INVENTION

The present invention describes a class of novel substituted pyridyl compounds useful as selective herbicides for use in agricultural practices. More particularly, the invention concerns substituted pyridyl compounds corresponding to the formula:

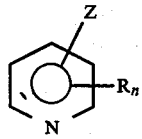

(I)

wherein Z is

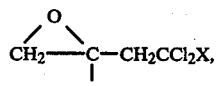

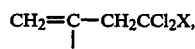

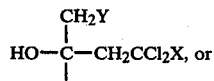

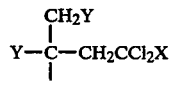

wherein X is hydrogen, chloro or methyl; Y is bromo or chloro; R is hydrogen, bromo, chloro, fluoro, $C_{1-4}$ alkyl, $C_{1-4}$ alkoxy, trifluoromethyl or nitro, and n is 1 or 2, with the proviso that at least one R substituent is other than hydrogen.

The compounds of the above Formula I, hereinafter referred to for convenience as "active ingredients", have been found to be uniquely active as herbicides for the control of undesired vegetation in certain crops. Accordingly, the present invention also encompasses compositions containing one or more active ingredients, as well as methods of controlling undesired plant growth. Such methods comprise applying one or more active ingredients to the locus of the undesired plants, that is, the seeds, foliage or other parts of the growing plants or soil in which the plants are growing or would grow.

DETAILED DESCRIPTION OF THE INVENTION

The term "alkyl" as used herein and in the appended claims is employed to designate the radicals methyl, ethyl, propyl, isopropyl, and the various butyl radicals. Similarly, the term "alkoxy" is employed to mean the radicals methoxy, ethoxy, propoxy, and isopropoxy and the isomeric butoxy radicals. The term "herbicide" is used herein to mean an active ingredient which controls or modifies the growth of plants.

The active ingredients of the present invention are generally oils or crystalline solids at ambient temperatures which are soluble in many organic solvents commonly employed as herbicidal carriers. The active ingredients of the above Formula I, wherein X is chloro and R is $CH_3$, Cl, Br or alkoxy, constitute a preferred embodiment of the present invention. The active ingredients, wherein X is chloro and R is chloro or methoxy, constitute the most preferred embodiments.

The active ingredients of the above Formula I wherein Z is

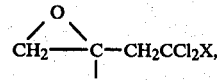

are readily prepared by the reaction of a substituted pyridine compound of the formula:

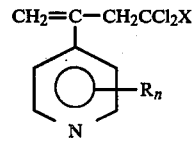

(II)

wherein X and R are as previously defined, with a suitable peracid reactant. Representative and suitable peracids which can be employed in the preparation of the active ingredients include, for example, perbenzoic acid and peracetic acid. In the present invention, buffer solutions of the acid reactants are preferably employed and are prepared by the use of a buffer agent, such as, for example, sodium acetate, or sodium benzoate.

In carrying out the reaction, the substituted pyridine reactant of Formula II in a reaction medium, such as, for example, methylene chloride, chloroform, carbon tetrachloride, or 1,2-dichlorobenzene, is mixed slowly with the peracid reactant in a buffer solution. While the amounts of the reactants to be employed are not critical, the reaction generally consumes reactants in the proportion of 1 mole of substituted pyridine reactant to 1 mole of acid reactant. However, an excess of acid reactant may be present to insure completion of the reaction. A suitable ratio of reactants is from about 1:1 to about 1:6 (substituted pyridine:acid) and the employment of the reactants in a mole ratio of from 1 to 3 is preferred. The reaction is usually conducted at temperatures between 25° and 100° C. and is ordinarily carried out at ambient atmospheric pressure. The resulting reaction mixture is usually maintained, with agitation, for a period of time sufficient to provide for substantial completion of the reaction. Generally, the reaction mixture is agitated at ambient temperatures for a period of from 24 to 100 hours or more. Recovery of the desired product from the reaction mixture is achieved by employing conventional separatory procedures. Typically, the reaction mass is washed with water and neutralized with a sufficient amount of a base, e.g., sodium carbonate or the like, before being concentrated to dryness under sub-atmospheric pressure.

The substituted pyridine reactants of Formula II can be easily prepared by those skilled in the art according to known methods or methods analagous thereto. For example, 2,6-dichloro-α,α-dimethyl-4-pyridinemethanol can be prepared by the Grignard reaction of methyl-2,6-dichloro-4-pyridinecarboxylate with methylmagnesiumiodide followed by acidification. Treatment of the methanol derivative with $P_2O_5$ removes water and forms 2,6-dichloro-4-isopropenylpyridine which may be reacted with $BrCCl_3$ in the presence of a cuprous chloride catalyst to give 2,6-dichloro-4-(1-bromo-3,3,3-trichloro-1-methylpropyl)pyridine which is then dehydrobrominated, e.g., by heating in the presence of a catalyst such as antimony pentachloride, aluminum chloride, cuprous chloride or a suitable base in an inert organic solvent to provide 2,6-dichloro-4-(3,3,3-trichloro-1-methylenepropyl)pyridine.

The compounds of the present invention have been found to be suitable for use in methods for the pre- and post-emergent control of weeds or other unwanted vegetation. Certain of the active ingredients of the present invention have been found to be active against undesired vegetation in the presence of desired crop plants while giving little or no herbicidal action on the crop plants. For all such uses, unmodified active ingredients of the present invention can be employed. However, the present invention embraces the use of a herbicidally-effective amount of the active ingredients in composition form with an inert agricultural carrier material in solid or liquid form. Thus, for example, an active ingredient can be dispersed on a finely divided solid and employed therein as a dust. Also, the active ingredients, as liquid concentrates or solid compositions comprising one or more of the active ingredients, can be dispersed in water, typically with the aid of a wetting agent, and the resulting aqueous dispersion employed as a spray. In other procedures, the active ingredient can be employed as a constituent of organic liquid compositions, oil-in-water and water-in-oil emulsions, or water dispersions, with or without the addition of wetting, dispersing, or emulsifying agents.

Organic solvents that can be employed as extending agents incude hydrocarbons, e.g. benzene, toluene, xylene, kerosene, diesel fuel, fuel oil, and petroleum naphtha; ketones such as acetone, methyl ethyl ketone, or cyclohexanone; chlorinated hydrocarbons such as carbon tetrachloride, chloroform, trichloroethylene, or perchloroethylene; esters such as ethyl acetate, amyl acetate, or butyl acetate; ethers e.g., ethylene glycol monomethyl ether and diethylene glycol monomethyl ether; alcohols, e.g., methanol, ethanol, isopropanol, amyl alcohol, ethylene glycol, propylene glycol, and glycerine. Mixtures of water and organic solvents, either as solutions or emulsions, can also be employed.

The active ingredients can further be applied as aerosols, e.g., by dispersing them by means of a compressed gas as known in the art.

The active ingredients of the present invention can also be applied with solid adjuvants or carriers such as talc, pyrophyllite, synthetic fine silica, attapulgus clay, kieselguhr, chalk, diatomaceous earth, lime, calcium carbonate, bentonite, fuller's earth, cottonseed hulls, wheat flour, soybean flour, pumice, tripoli, wood flour, walnut shell flour, redwood flour, or lignin.

As stated, it is frequently desirable to incorporate a surface active agent in the compositions of the present invention. Such surface active or wetting agents are advantageously employed in both the solid and liquid compositions. The surface active agent can be anionic, cationic or nonionic in character.

Typical classes of surface active agents include alkyl sulfonate salts, alkylaryl sulfonate salts, alkylaryl polyether alcohols, fatty acid esters or polyhydric alcohols and the alkylene oxide addition products of such esters, and addition products of long chain mercaptans and alkylene oxides. Typical examples of such surface active agents include the sodium alkylbenzene sulfonates having 10 to 18 carbon atoms in the alkyl group, alkylphenol-ethylene oxide condensation products, e.g., p-isooctylphenol condensed with 10 ethylene oxide units, soaps, e.g., sodium stearate and potassium oleate, sodium salt of propylnaphthalene sulfonic acid, di(2-ethylhexyl)ester of sodium sulfosuccinic acid, sodium lauryl sulfate, sodium decanesulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, sodium N-methyl-N-oleyl taurate, Turkey Red Oil, sodium dibutyl naphthalene sulfonate, sodium lignin sulfonate, polyethylene glycol stearate, tertiary dodecyl polyethylene glycol thioether, long chain ethylene oxide-propylene oxide condensation products, e.g., molecular weight 1000, polyethylene glycol ester of tall oil acids, sodium octyl phenoxyethoxyethyl sulfate, tris(polyoxyethylene)sorbitan monostearate, and sodium dihexyl sulfosuccinate.

The concentration of the active ingredients in solid or liquid compositions generally is from about 0.003 to about 95 percent by weight. Concentrations of from about 0.003 to 50 weight percent are often employed. In compositions to be employed as concentrates, the active ingredient can be present in a concentration of from about 5 to about 98 weight percent. The active ingredient compositions can also contain other compatible additaments, for example, phytotoxicants, plant growth regulants, and pesticides, and can be formulated with solid particulate fertilizer carriers such as ammonium nitrate or urea.

Such additional pesticidal compounds may be insecticides, nematocides, arthropodicides, herbicides, fungicides or bactericides that are compatible with the compounds of the present invention in the medium selected for application and not antagonistic to the activity of the present compounds. Accordingly, in such embodiments, the pesticidal compound is employed as a supplemental toxicant for the same or for a different pesticidal use or as an additament. The compounds in combination can generally be present in the ratio of from 1 to 100 parts of the compound of the present invention with from 100 to 1 parts of the additional compound(s). The compounds of this invention are advantageously employed in combination with herbicides that are used in corn, soybeans, cotton and sorghum.

The present compositions can be applied by the use of power-dusters, boom and hand sprayers, spray-dusters, by addition to irrigation water, and by other conventional means. The compositions can also be applied from airplanes as a dust or a spray.

The active ingredients of the present invention have been found to possess particularly unique and desirable herbicidal activity against undesired plants, including crabgrass, barnyard grass and yellow foxtail and especially in pre-emergence operations. Such unique herbicidal activity is obtained at various low, economical application rates without endangering desirable crop species, such as, for example, cotton, corn, sorghum or soybeans.

The exact rate to be applied is dependent not only upon the specific active ingredient being employed, but also upon the particular action desired (e.g., general or selective control), the plant species to be modified and the stage of growth thereof as well as the part of the plant to be contacted with the toxic active ingredient. Thus, all of the active ingredients of the invention and compositions containing the same may not be equally effective at similar concentrations or against the same plant species. In non-selective pre-emergence and foliage treatments, the active ingredients of this invention are usually applied at an approximate rate of from about 1 to about 25 lbs. per acre, (1.12–27.8 kg/hectate), but lower or higher rates may be appropropriate in some cases. In selective pre- and post-emergence operations, a dosage of from about 0.13 to about 1.0 pounds per acre (0.145–1.12 kg/hectare) is usually employed, but higher dosages may be necessary in some instances. One skilled in the art can readily determine the optimum rate to be applied in any particular case.

The following examples further illustrate the present invention.

EXAMPLE 1

Preparation of 2,6-dichloro-4-(2-(2,2,2-trichloroethyl)oxiranyl)pyridine

Method A

In a 50-ml flask was dissolved 0.57 g (0.0019 mole) of 2,6-dichloro-4-(3,3,3-trichloro-1-methylenepropyl)pyridine in 25 ml of carbon tetrachloride. To the solution was added 0.387 g (0.0019 mole) of 85% m-chloroperbenzoic acid and the reaction mixture heated at reflux for 48 hrs. Another 0.20 g of m-chloroperbenzoic acid was added and reflux continued for 30 hrs. The reaction mixture was cooled to room temperature and worked up by adding 50 ml of carbon tetrachloride and washing the mixture with 50 ml of 10% aqueous sodium bisulfite, 10% aqueous sodium carbonate (3×50 ml) and 50 ml of water. The organic layer was dried (Na$_2$SO$_4$) and solvent removed in vacuo leaving 0.59 g of crude product. The product was purified by column chromatography by placing the material on 80 g of silica gel and eluting with a solution of hexane and acetone. A fraction of 0.32 g of desired product was obtained and shown to be 97% by nuclear magnetic resonance spectroscopy.

Method B (preferred)

A solution of 4.0 g (13.1 mmoles) of 2,6-dichloro-2-(3,3,3-trichloro-1-methylenepropyl)pyridine and 2.81 g (80%, 13.1 mmoles) of m-chloroperoxybenzoic acid in 35 ml of CDCl$_3$ was refluxed for 18 hours at which time 2.0 g (14.5 mmoles) of additional m-chloroperoxybenzoic acid (80%) was added and reflux continued for six hours. The reaction mixture was cooled, filtered and the filtrate diluted with CH$_2$Cl$_2$ and washed with 5% NaHSO$_3$, 7% NaOH, dried (MgSO$_4$) and concentrated in vacuo. The crude product was dissolved in a hot mixture (7:3) of hexane and ether and undissolved impurities removed by filtration. After evaporation of the solvent, the product, 1.5 g (36%), was further purified by trituration in 5% ether in pentane, m.p. 92°–95° C.

EXAMPLE 2

Preparation of 2-chloro-6-methoxy-4-(2-(2,2,2-trichloroethyl)oxiranyl)pyridine

Step I. Preparation of methyl-2,6-dichloroisonicotinate

A solution of 187 g (0.974 mole) of 2,6-dichloroisonicotinic acid, 1650 ml of methanol and 5 ml of concentrated sulfuric acid was heated at reflux for 24 hours. Most of the solvent was removed in vacuo, leaving crude product which was dissolved in 750 ml of methylene chloride and washed with water and 1N sodium hydroxide. The organic layer was dried (Na$_2$SO$_4$) and solvent removed in vacuo affording 174 g (86.7% yield) of methyl 2,6-dichloroisonicotinate, m.p. 79°–81° C.

Step II. Preparation of methyl-2-methoxy-6-chloroisonicotinate

To a solution of 20.7 g (0.901 mole) of sodium metal dissolved in 1.0 liter of methanol was added 168.8 g (0.819 mole) of methyl 2,6-dichloroisonicotinate. The solution was heated at reflux for one hour. The reaction mixture was cooled and diluted with a solution of 50 ml of concentrated hydrochloric acid dissolved in 1.0 liter of water with the product crystallizing out of solution. The methyl-2-chloro-6-methoxyisonicotinate was collected by filtration, washed with water and dried in vacuo to constant weight, 156.3 g (94.7% yield), m.p. 97.5°–101° C.

Step III. Preparation of 2-chloro-6-methoxy-α,α-dimethyl-4-pyridinemethanol

To a solution of 155.7 g (0.772 mole) of methyl-2-chloro-6-methoxyisonicotinate dissolved in 2.0 liter of benzene was added a solution of 563 ml of 3.0M methyl magnesium bromide in diethyl ether (1.69 moles) dropwise over one hour. The slurry was heated at reflux for 1.5 hours and cooled to 10° C. in an ice bath. To the cold slurry was added dropwise a solution of 300 ml of concentrated hydrochloric acid dissolved in 1200 ml of water. The mixture was allowed to warm to room temperature and the organic layer separated and washed with water, 1N sodium hydroxide and dried (Na$_2$SO$_4$). Removal of solvent in vacuo afforded 142.3 g (91.4% yield) of desired 2-chloro-6-methoxy-α,α-dimethyl-4-pyridinemethanol.

Step IV. Preparation of 2-chloro-6-methoxy-4-(1-methylethenyl)pyridine

To a solution of 131.5 g (0.652 mole) of 2-chloro-6-methoxy-α,α-dimethyl-4-pyridinemethanol dissolved in 1.0 liter of acetonitrile was added 105 g (0.685 mole) of phosphoryl chloride. The solution was heated at reflux for 11 hours and most of the solvent removed in vacuo. The residue remaining was dissolved in 700 ml of carbon tetrachloride and poured over ice and water. The mixture was made basic with potassium carbonate and the organic layer separated and washed with additional aqueous potassium carbonate. The organic layer was dried (Na2SO4) and solvent removed in vacuo yielding 110.8 g (92.5% yield) of desired product. Distillation afforded 96 g (80% yield) of pure 2-chloro-6-methoxy-4-(1-methylethenyl)pyridine, b.p. 99°–102° C./2.0 mm.

Step V. Preparation of 2-chloro-6-methoxy-4-(1-bromo-3,3,3-trichloro-1-methylpropyl)pyridine

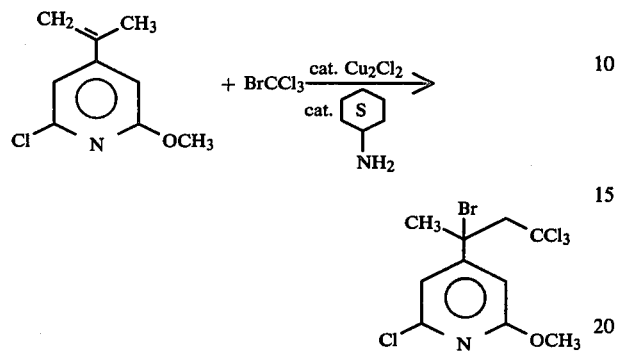

To a solution of 90 g (0.49 mole) of 2-chloro-6-methoxy-4-(1-methylethenyl)pyridine dissolved in 248 ml of bromotrichloromethane was added 0.24 g of cuprous chloride and 1.0 g of cyclohexylamine. The slurry was heated at reflux for 15 minutes and cooled. The mixture was diluted with 200 ml of methylene chloride and the copper catalyst removed by filtration. The filtrate was washed with aqueous hydrochloric acid, dried (Na2SO4) and solvent removed in vacuo, yielding 180.9 g (96.6% yield) of crystalline 2-chloro-6-methoxy-4-(1-bromo-3,3,3-trichloro-1-methylpropyl)pyridine. Recrystallization from hexane afforded pure product, m.p. 52°–53.5° C.

Analysis for $C_{10}H_{10}BrCl_4NO$; mol. wt. 381.932. Calc'd: %C, 31.44; %H, 2.64; %N, 3.67. Found: %C, 31.3; %H, 2.80; %N, 3.72.

Step VI. Preparation of 2-chloro-6-methoxy-4-(3,3,3-trichloro-1-methylenepropyl)pyridine

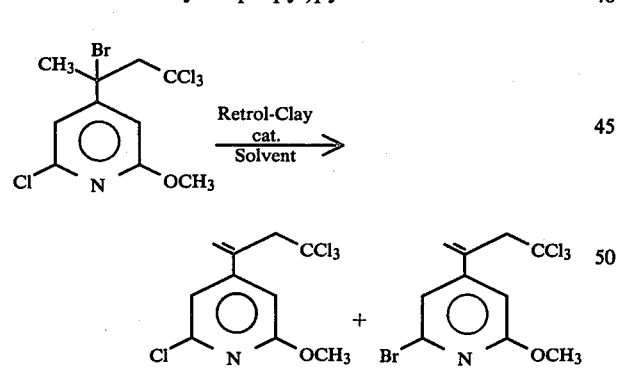

To a solution of 50 g (0.131 mole) of 2-chloro-6-methoxy-4-(1-bromo-3,3,3-trichloro-1-methylpropyl)-pyridine dissolved in 500 ml of O-dichlorobenzene was added 5.0 g of Retrol-Clay catalyst, Grade 6 (finely divided clay catalyst obtained from Filtrol Corp.) The slurry was heated at reflux for 5.5 hours, cooled, and the slurry filtered through Celite ® to remove the catalyst. The solvent was removed in vacuo, leaving 36.3 g of crude product. Purification was accomplished via column chromatography on silica gel using 3% ethyl acetate—97% hexane as eluent. 12.8 g of desired 2-chloro-6-methoxy-4-(3,3,3-trichloro-1-methylenepropyl)pyridine containing 2-bromo-6-methoxy-4-(3,3,3-trichloro-1-methylenepropyl)pyridine was obtained.

Step VII. Preparation of 2-chloro-6-methoxy-4-(2-(2,2,2-trichloroethyl)oxiranyl)pyridine

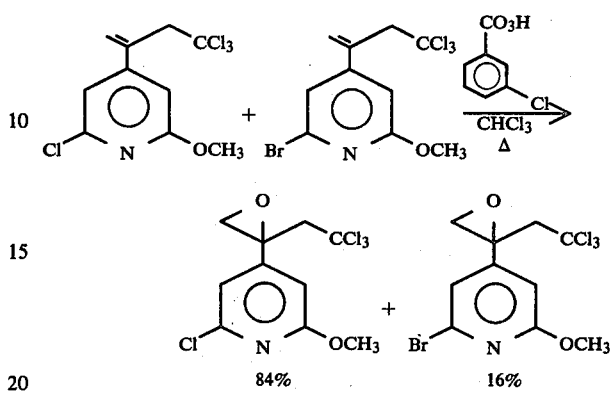

To a solution of 11.8 g of 2-chloro-6-methoxy-4-(3,3,3-trichloro-1-methylenepropyl)pyridine containing the 2-bromo-6-methoxy-4-(3,3,3-trichloro-1-methylenepropyl)pyridine byproduct in 300 ml of chloroform was added 10.3 g of 85% m-chloro-perbenzoic acid. The solution was heated at reflux for 32 hours, cooled, and washed with 2N sodium hydroxide, water, and dried (Na2SO4). The solvent was removed in vacuo, leaving 12.5 g of crude product which was purified by high pressure liquid chromatography using 5% ethyl acetate in hexane as eluent. 5.4 g of pure product containing 16% of the bromo derivative was obtained. Analysis of the mixture was confirmed by gas-liquid chromatography, nuclear magnetic resonance spectroscopy, mass spectroscopy, and elemental analysis. Elemental analysis for the mixture:

Calc'd: %C, 37.2; %H, 2.81; %N, 4.34. Found: %C, 37.0; %H, 2.82; %N, 4.45.

EXAMPLE 3

Preparation of 2-chloro-5-(3,3,3-trichloro-1-methylenepropyl)pyridine

Step I. Preparation of 2-chloro-5-(1-methylethenyl)-pyridine

A solution of 1.0 liter of xylene (b.p. 130°–141° C.), 172.4 g (1 mole) of 6-chloro-α,α-dimethyl-3-pyridinemethanol and 10 g (0.053 mole) of para toluenesulfonic acid monohydrate was heated at reflux for three hours and the water byproduct was collected in a Dean-Stark trap. The mixture was cooled to room temperature and washed with 0.5M Na2CO3 and dried (MgSO4). Solvent was removed under vacuum. The product (119 g, 77%) was obtained by distillation, b.p. 70°–78° C. at 0.5–0.9 mm, $N_d=1.5584$.

|   | Calc'd | Found |
|---|--------|-------|
| C | 62.55  | 61.85 |
| H | 5.25   | 5.13  |
| N | 9.12   | 8.94  |

Step II. Preparation of 2-chloro-5-(1,3,3,3-tetrachloro-1-methylpropyl)pyridine 67.3 g (0.44 mole) of 2-chloro-5-(1-methylethenyl)-pyridine as added to a refluxing slurry of 2.0 g (20 mmoles) of cyclohexylamine and 0.5 g (5 mmoles) of finely divided CuCl in 500 ml of CCl4. After 3.5 hours at reflux, the reaction mixture was cooled and poured through a 3 inch bed of silica gel and the bed was washed with 500 ml of ether. The solvent was removed under vacuum and the product recrystallized from hexane. The yield was 93.3 g (69%), m.p. 80.5°–81° C.

|   | Calc'd | Found |
|---|--------|-------|
| C | 35.16  | 35.03 |
| H | 2.62   | 2.49  |
| N | 4.56   | 4.57  |

Step III. Preparation of 2-chloro-5-(3,3,3-trichloro-1-methylenepropyl)pyridine

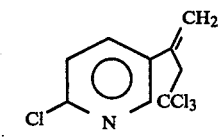

A solution of 40 g (0.013 mole) of 2-chloro-5-(1,3,3,3-tetrachloro-1-methylpropyl)pyridine and 7.8 g (0.026 mole) of $SbCl_5$ in 300 ml of chlorobenzene was heated to 138° C. for one hour. The darkened solution was cooled and carefully quenched with water. The heterogeneous mixture was filtered, the organic layer separated, dried ($MgSO_4$) and concentrated in vacuo. The product was crystallized from 350 ml of pentane at −50° C. The yield was 19.5 g (55%), m.p. 54°–55° C.

EXAMPLE 4

Preparation of (A) 5-(1-bromo-1-(bromomethyl)-3,3,3-trichloropropyl)-2-chloropyridine and (B) α-(bromomethyl)-6-chloro-α-(2,2,2-trichloroethyl)-3-pyridine methanol 3.2 g (20 mmoles) of bromine was added to a solution of 5.4 g (20 mmoles) of 2-chloro-5-(3,3,3-trichloro-1-methylenepropyl)pyridine in 11 ml of dioxane and 10 ml of water and the mixture was stirred for one hour at 25° C. 100 ml of ether was added, the water layer removed and the organic layer washed with aqueous $Na_2CO_3$, separated, dried ($MgSO_4$) and concentrated in vacuo. Purification via high pressure liquid chromatography using a solution of 20% acetone and 80% hexane as eluent afforded both products (A) and (B). An amber oil, identified by NMR as (A) was eluted first as the major product. 1.3 g (18%) of (B), m.p. 96°–100° C. was additionally obtained as the second product.

EXAMPLE 5

Preparation of 2-chloro-5-(2-(2,2,2-trichloroethyl)oxiranyl)pyridine

To a solution of 7.0 g (19 mmoles) of α-(bromomethyl)-6-chloro-α-(2,2,2-trichloroethyl)-3-pyridinemethanol in 200 ml of acetonitrile was added 10 g (0.07 mole) of powdered anhydrous $K_2CO_3$. The slurry was stirred for five minutes, filtered and the filtrate concentrated in vacuo, giving 5 g of crude product. Recrystallization from hexane yielded 3.6 g (66%) of product, m.p. 65°–67° C.

EXAMPLE 6

Preparation of 2-chloro-6-(3,3,3-trichloro-1-methylenepropyl)pyridine 5.0 g (14.2 mmoles) of 6-chloro-2-(1-bromo-3,3,3-trichloro-1-methylpropyl)pyridine, which was prepared by the method of Example 1 using appropriate starting materials, was vaporized at 130°–230° C. and 1.0 mm of pressure and passed through a hot tube containing silica gel. The product was collected in a cold trap, dissolved in $CH_2Cl_2$, washed with water and aqueous sodium carbonate. The organic layer was separated, dried ($MgSO_4$) and concentrated to 1.2 g (31%) of clear oil which crystallized upon standing, m.p. 42°–45° C.

EXAMPLE 7

Preparation of 2,6-dichloro-4-(3,3,3-trichloro-1-methylenepropyl)pyridine

Step I. Preparation of 2,6-dichloroisonicotinic acid monohydrate

A solution of 750 g (2.83 moles) of 2,6-dichloro-4-trichloromethylpyridine in 1.0 liter of 85% $H_2SO_4$ was heated at 160° C. for three hours. The solution was cooled and added to 5.0 liters of ice water. The resulting crude crystalline product was separated and dissolved in 1:1 ether:acetone, dried ($MgSO_4$) and the solvent removed in vacuo to yield 508 g (85%) product, m.p. 208°–210° C.

Step II. Preparation of methyl-2,6-dichloroisonicotinate

To 1.5 liters of dry benzene was added 700 g (5.88 moles) of thionyl chloride, 1.0 ml dimethylformamide (DMF) and then slowly 508 g of 2,6-dichloroisonicotinic acid monohydrate. The slurry was heated at reflux for four hours and the resulting solution cooled to 40°–50° C. 200 ml of methanol was added dropwise to maintain at temperature of 75° C. The solvent was removed in vacuo. Recrystallization from hexane yielded 461 g (93%) of product, m.p. 81°–82° C.

Step III. Preparation of 2,6-dichloro-α,α-dimethyl-4-pyridinemethanol

A benzene solution of 420 g (2.1 moles) of methyl 2,6-dichloroisonicotinate was added dropwise to a freshly prepared solution of methyl magnesium iodide (4.6 moles) in 2.5 liters of anhydrous ether at such a rate to maintain reflux. After addition was completed, the mixture was refluxed an additional 10 minutes and then cooled. A solution of aqueous $NH_4Cl$ was added slowly, followed by the addition of concentrated HCl to dissolve the magnesium salts. The organic layer was separated, dried ($MgSO_4$) and concentrated in vacuo to yield 413.5 g (96%) of the desired product, which crystallized upon standing, m.p. 82°–83° C.

Step IV. Preparation of 2,6-dichloro-4-(1-methylethenyl)pyridine 75 g of $P_2O_5$ was added to 500 g of 98% methanesulfonic acid and the mixture heated at 100°–125° C. to obtain a homogeneous solution. The solution was cooled to 90° C., 70 g (0.34 mole) of 2,5-dichloro-α,α-dimethyl-4-pyridinemethanol was added and the temperature was maintained at 90° C. for two hours. The solution was cooled and slowly poured over 2.0 liters of ice and water. The organic layer was extracted with ether, dried ($MgSO_4$) and concentrated in vacuo. Distillation gave 62.6 g (91%) of the desired olefin, b.p. 80° C. at 0.05 mm.

Step V. Preparation of 4-(1-bromo-3,3,3-trichloro-1-methylpropyl)-2,6-dichloropyridine 51 g of 2,6-dichloro-4-(methylethenyl)pyridine was added to a slurry of 0.54 (5.5 mmoles) of cyclohexylamine and 0.2 g (1.4 mmoles) of finely divided CuBr in 750 g of $BrCCl_3$ at a rate such that the temperature was maintained at 50°-90° C. The mixture was heated an additional hour at $\leq$90° C., cooled and filtered through a 3 inch bed of silica gel. The bed was washed with ether and the organic layer concentrated in vacuo. Recrystallization from pentane at −40° C. yielded 91 g (87%) of product, m.p. 51°-55° C.

Step VI. Preparation of 2,6-dichloro-4-(3,3,3-trichloro-1-methylenepropyl)pyridine To a dried tetrahydrofuran solution of 4.03 g of 2,2,6,6-tetramethylpiperidine under $N_2$ was added 17.8 ml of 1.6M n-butyllithium in hexane. The solution was cooled to −75° C. and a concentrated solution of 4-(1-bromo-3,3,3-trichloro-1-methylpropyl)-2,6-dichloropyridine in tetrahydrofuran was added to maintain $\leq$ −65° C. The mixture was stirred at −65° C. for two hours and quenched with 20 mls of water. The organics were extracted with ether, dried ($MgSO_4$), and concentrated in vacuo. The crude product was purified via high pressure liquid chromatography, yielding 5 g (68%), m.p. 66°-67.5° C.

EXAMPLE 8

Preparation of 2,3-dichloro-5-(3,3,3-trichloro-1-methylenepropyl)pyridine

To a slurry of 5 g of neutral alumina in 300 ml of carbon tetrachloride was added 0.5 g of anhydrous aluminum chloride and the mixture was heated at reflux for 20 minutes. To the slurry was added 20 g (0.052 mole) of 2,3-dichloro-5-(1-bromo-3,3,3-trichloro-1-methylpropyl)pyridine, and the resulting mixture was heated at reflux for 48 hours. The mixture was cooled and filtered. The filtrate was concentrated in vacuo yielding the crude product. Recrystallization from pentane yielded 12.7 g (80%) of product, m.p. 76°-77° C.

EXAMPLE 9

Preparation of 3,6-dichloro-2-(3,3,3-trichloro-1-methylenepropyl)pyridine

A slurry of 15 g (0.039 mole) of 3,6-dichloro-2-(1-bromo-3,3,3-trichloro-1-methylpropyl)pyridine and 5 g of finely divided CuCl in O-dichlorobenzene was washed at reflux for two hours. The mixture was cooled, filtered and the filtrate concentrated in vacuo. Recrystallization from pentane yielded 4.5 g (38%) of product, m.p. 71°-74° C.

Following the above procedures and starting with the appropriate starting materials, the following compounds were prepared:

| Compound | Data |
|---|---|
| Cl-pyridine with $CH_2CCl_3$ and $H_2C$-O-C group (Cl, Cl, N) | Structure confirmed by NMR |
| Cl-pyridine with $CH_2CCl_3$ and $H_2C$-O-C group | M.P. 60°-62° C. |
| Cl-pyridine (Cl, Cl) with $CH_2CCl_3$ and $CH_2$=C | $N_{d25}$ 1.5848 |
| Cl-pyridine (Cl, Cl) with $CH_2CCl_3$ and $CH_2$-O-C | Structure confirmed by NMR |
| Cl-pyridine (Cl, Cl) with $CH_2CCl_3$ and $CH_2$-O-C | $N_{d25}$ 1.5715 |
| $F_3C$-pyridine with $CH_2CCl_2$ and $CH_2$-O-C | M.P. 43°-45° C. |

EXAMPLE 10

In representative operations, each compound to be utilized in a series of tests is dissolved in acetone to ½ the final volume (twice the final concentration) to be used and the acetone solution in each case is admixed with an equal volume of water containing 0.1 percent by weight of surface active material. The compositions, generally in the nature of an emulsion, were employed to treat separate respective seed beds of sandy loam soil of good nutrient content wherein each seed bed contained separate groups of viable seeds, each group being of one plant specie. The various beds were positioned side by side and exposed to substantially identical conditions of temperature and light. Each bed was maintained so as to prevent any interaction with test compounds in different seed beds. Each seed bed was treated with one of the compositions as a soil drench applied uniformly throughout the surface of the bed. The compositions were applied to the seed beds so that different seed beds of a given plant specie were treated with one of each of the test compounds. Another seed bed was treated only with water to serve as a control. After treatment, the seed beds were maintained for two weeks under greenhouse conditions conducive for good plant growth and watered as necessary. The specific plant specie, test compound and dosage and the percent preemergent control obtained are set forth in the table below. Control refers to the reduction in growth compared to the observed results of the same specie.

PREEMERGENCE CONTROL OF PLANT SPECIES

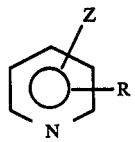

| Compound tested | | | Dosage in Pounds/Acre | | | | | | |
|---|---|---|---|---|---|---|---|---|---|
| R | Z | Plant Species | 4.0 | 2.0 | 1.0 | 0.5 | 0.25 | 0.125 | 0.063 |
| 2-Cl | 5-BrCH$_2$—C(OH)—CH$_2$CCl$_3$ | Barnyardgrass | NT | NT | 100 | 90 | 70 | 10 | 0 |
| | | Crabgrass | NT | NT | 100 | 100 | 95 | 40 | 20 |
| | | Foxtail | NT | NT | 60 | 20 | 0 | 0 | 0 |
| | | Johnsongrass | NT | NT | 95 | 95 | 20 | 0 | 0 |
| | | Wild Oats | NT | NT | 100 | 70 | 0 | 0 | 0 |
| 2-Cl | 5-CH$_2$=C—CH$_2$CCl$_3$ | Barnyardgrass | 99 | 95 | 85 | 20 | 0 | NT | NT |
| | | Crabgrass | 100 | 100 | 100 | 99 | 90 | NT | NT |
| | | Foxtail | 70 | 90 | 75 | 30 | 0 | NT | NT |
| | | Johnsongrass | 80 | 90 | 70 | 50 | 10 | NT | NT |
| | | Wild Oats | 70 | 50 | 20 | 10 | 0 | NT | NT |
| 2-Cl | 5-BrCH$_2$—C(Br)—CH$_2$CCl$_3$ | Barnyardgrass | 100 | 95 | 80 | 15 | 0 | NT | NT |
| | | Crabgrass | 100 | 100 | 95 | 100 | 95 | NT | NT |
| | | Foxtail | 99 | 95 | 0 | 0 | 0 | NT | NT |
| | | Johnsongrass | 90 | 99 | 20 | 0 | 0 | NT | NT |
| | | Wild Oats | 40 | 20 | 20 | 0 | 0 | NT | NT |
| 2,3-diCl | 5-CH$_2$—C(O epoxide)—CH$_2$CCl$_3$ | Barnyardgrass | 100 | 100 | 100 | 100 | 35 | NT | NT |
| | | Crabgrass | 100 | 100 | 100 | 20 | 0 | NT | NT |
| | | Foxtail | 100 | 99 | 75 | 0 | 0 | NT | NT |
| | | Johnsongrass | 100 | 100 | 100 | 30 | 30 | NT | NT |
| | | Wild Oats | 100 | 20 | 20 | 20 | 0 | NT | NT |
| 2-Cl | 6-CH$_2$—C(O epoxide)—CH$_2$CCl$_3$ | Barnyardgrass | NT | NT | 100 | 100 | 100 | 100 | 0 |
| | | Crabgrass | NT | NT | 100 | 100 | 100 | 40 | 0 |
| | | Foxtail | NT | NT | 100 | 100 | 100 | 60 | 15 |
| | | Johnsongrass | NT | NT | 100 | 100 | 100 | 50 | 15 |
| | | Wild Oats | NT | NT | 100 | 100 | 100 | 99 | 100 |
| 2,3-diCl | 5-CH$_2$=C—CH$_2$CCl$_3$ | Barnyardgrass | 80 | 60 | 10 | 0 | 0 | NT | NT |
| | | Crabgrass | 80 | 80 | 0 | 0 | 0 | NT | NT |
| | | Foxtail | 85 | 50 | 10 | 10 | 0 | NT | NT |
| | | Johnsongrass | 85 | 70 | 65 | 10 | 0 | NT | NT |
| | | Wild Oats | 95 | 90 | 30 | 10 | 0 | NT | NT |
| 2,5-diCl | 6-CH$_2$=C—CH$_2$CCl$_3$ | Barnyardgrass | 75 | 60 | 0 | 0 | 0 | NT | NT |
| | | Crabgrass | 80 | 80 | 0 | 0 | 0 | NT | NT |
| | | Foxtail | 65 | 40 | 0 | 0 | 0 | NT | NT |
| | | Johnsongrass | 60 | 15 | 15 | 0 | 0 | NT | NT |
| | | Wild Oats | 50 | 50 | 50 | 0 | 0 | NT | NT |
| 2,5-diCl | 6-CH$_2$—C(O epoxide)—CH$_2$CCl$_3$ | Barnyardgrass | 100 | 100 | 100 | 95 | 0 | NT | NT |
| | | Crabgrass | 100 | 100 | 100 | 90 | 25 | NT | NT |
| | | Foxtail | 100 | 100 | 100 | 50 | 15 | NT | NT |
| | | Johnsongrass | 100 | 100 | 100 | 30 | 30 | NT | NT |
| | | Wild Oats | 100 | 100 | 100 | 40 | 30 | NT | NT |
| 2-Cl | 6-CH$_2$=C—CH$_2$CCl$_3$ | Barnyardgrass | NT | 100 | 100 | 100 | 90 | 40 | NT |
| | | Crabgrass | NT | 90 | 85 | 70 | 0 | 0 | NT |
| | | Foxtail | NT | 90 | 70 | 35 | 15 | 0 | NT |
| | | Johnsongrass | NT | 100 | 95 | 95 | 35 | 0 | NT |
| | | Wild Oats | NT | 100 | 99 | 90 | 50 | 50 | NT |

-continued
PREEMERGENCE CONTROL OF PLANT SPECIES

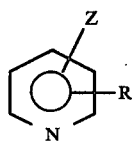

| Compound tested | | | Dosage in Pounds/Acre | | | | | | |
|---|---|---|---|---|---|---|---|---|---|
| R | Z | Plant Species | 4.0 | 2.0 | 1.0 | 0.5 | 0.25 | 0.125 | 0.063 |
| 2,4-diCl | 6-CH₂=C—CH₂CCl₃ | Barnyardgrass | NT | 100 | 80 | 15 | 0 | 0 | NT |
| | | Crabgrass | NT | 100 | 98 | 100 | 70 | 60 | NT |
| | | Foxtail | NT | 70 | 55 | 0 | 0 | 0 | NT |
| | | Johnsongrass | NT | 20 | 15 | 0 | 0 | 0 | NT |
| | | Wild Oats | NT | 25 | 10 | 0 | 0 | 0 | NT |
| 2-CF₃ | 6-CH₂—C(O)—CH₂CCl₃ (epoxide) | Barnyardgrass | NT | NT | 100 | 90 | 35 | 0 | NT |
| | | Crabgrass | NT | NT | 60 | 30 | 0 | 0 | NT |
| | | Foxtail | NT | NT | 80 | 35 | 0 | 0 | NT |
| | | Johnsongrass | NT | NT | 60 | 20 | 0 | 0 | NT |
| | | Wild Oats | NT | NT | 100 | 70 | 30 | 0 | NT |
| 2,4-diCl | 6-CH₂—C(O)—CH₂CCl₃ (epoxide) | Barnyardgrass | NT | NT | 100 | 100 | 100 | 100 | 40 |
| | | Crabgrass | NT | NT | 100 | 100 | 100 | 98 | 70 |
| | | Foxtail | NT | NT | 100 | 100 | 98 | 95 | 35 |
| | | Johnsongrass | NT | NT | 75 | 75 | 55 | 20 | 0 |
| | | Wild Oats | NT | NT | 100 | 80 | 50 | 10 | 0 |
| 6-Cl 2-OCH₃ | 4-CH₂—C(O)—CH₂CCl₃ (epoxide) | Barnyardgrass | NT | NT | 100 | 100 | 100 | 95 | 0 |
| | | Crabgrass | NT | NT | 100 | 100 | 100 | 100 | 100 |
| | | Foxtail | NT | NT | 100 | 100 | 90 | 50 | 0 |
| | | Johnsongrass | NT | NT | 99 | 65 | 40 | 0 | 0 |
| | | Wild Oats | NT | NT | 100 | 70 | 60 | 10 | 0 |
| 2-Cl | 5-CH₂—C(O)—CH₂CCl₃ (epoxide) | Barnyardgrass | NT | NT | 100 | 100 | 95 | 85 | 0 |
| | | Crabgrass | NT | NT | 100 | 99 | 90 | 60 | 0 |
| | | Foxtail | NT | NT | 90 | 40 | 0 | 0 | 0 |
| | | Johnsongrass | NT | NT | 50 | 30 | 10 | 0 | 0 |
| | | Wild Oats | NT | NT | 10 | 0 | 0 | 0 | 0 |
| 2,6-diCl | 4-CH₂—C(O)—CH₂CCl₃ (epoxide) | Barnyardgrass | NT | NT | 100 | 100 | 100 | 100 | 50 |
| | | Crabgrass | NT | NT | 100 | 100 | 100 | 99 | 85 |
| | | Foxtail | NT | NT | 100 | 100 | 99 | 85 | 20 |
| | | Johnsongrass | NT | NT | 105 | 100 | 40 | 10 | 0 |
| | | Wild Oats | NT | NT | 100 | 98 | 50 | 40 | 10 |

NT = Not Tested

EXAMPLE 11

To illustrate the phytotoxic properties of the various active ingredients of the present invention in postemergent application, a group of controlled greenhouse experiments is described below.

Various species of plants were planted in beds of good agricultural soil in a greenhouse. After the plants had emerged and grown to a height of about 1–6 inches (5–15 cm), a portion of the plants were sprayed with an aqueous mixture, made by mixing a selected active ingredient and emulsifier or dispersant with about 1:1 water:acetone, employing sufficient amounts of the treating composition to provide application rates of 4000 parts per million (ppm) or about 10 pounds per acre (11.2 kg/hectare) and in some cases at lower rates. Other portions of the plants were left untreated to serve as controls.

After two weeks, the effect of the respective test ingredients used in respective groups of plants was evaluated by a comparison with the control groups of the plants. The results are tabulated in the following table.

POSTEMERGENCE CONTROL OF PLANT SPECIES

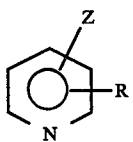

| Compound Tested | | | Dosage in PPM | | | | | |
|---|---|---|---|---|---|---|---|---|
| R | Z | Plant Species | 1000 | 500 | 250 | 125 | 62.5 | 31.25 |
| 2-Cl; 6-OCH₃ | 4-H₂C—C(O)—CH₂CCl₃ | Barnyardgrass | 85 | 85 | 85 | 80 | 75 | 50 |
| | | Crabgrass | 90 | 90 | 90 | 90 | 90 | 85 |
| | | Foxtail | 95 | 90 | 85 | 90 | 95 | 80 |
| | | Johnsongrass | 70 | 50 | 40 | 25 | 0 | NT |
| | | Wild Oats | 80 | 60 | 55 | 40 | 40 | 10 |
| 2-Cl | 6-CH₂=C—CH₂CCl₃ | Barnyardgrass | 40 | 0 | 0 | 0 | NT | NT |
| | | Crabgrass | 70 | 75 | 70 | 0 | NT | NT |
| | | Foxtail | 65 | 80 | 20 | 0 | NT | NT |
| | | Johnsongrass | 30 | 0 | 0 | 0 | NT | NT |
| 2,4-diCl | 6-CH₂=C—CH₂CCl₃ | Barnyardgrass | 0 | 0 | 0 | 0 | 0 | NT |
| | | Crabgrass | 80 | 65 | 60 | 60 | 0 | NT |
| | | Foxtail | 60 | 40 | 0 | 0 | 0 | NT |
| | | Johnsongrass | 10 | 0 | 0 | 0 | 0 | NT |
| | | Wild Oats | 0 | 0 | 0 | 0 | 0 | NT |
| 2-CF₂ | 6-CH₂—C(O)—CH₂CCl₃ | Barnyardgrass | 75 | 50 | 25 | 0 | NT | NT |
| | | Crabgrass | 0 | 0 | 0 | 0 | NT | NT |
| | | Foxtail | 0 | 0 | 0 | 0 | NT | NT |
| | | Johnsongrass | 0 | 0 | 0 | 0 | NT | NT |
| | | Wild Oats | 60 | 10 | 0 | 0 | NT | NT |
| 2-Cl | 6-CH₂—C(O)—CH₂CCl₃ | Barnyardgrass | 80 | 80 | 70 | 50 | 10 | 0 |
| | | Crabgrass | 80 | 70 | 60 | 55 | 10 | 0 |
| | | Foxtail | 85 | 80 | 75 | 45 | 0 | 0 |
| | | Johnsongrass | 50 | 10 | 0 | 0 | 0 | 0 |
| | | Wild Oats | 20 | 20 | 0 | 0 | 0 | 0 |
| 2,3-diCl | 5-CH₂—C(O)—CH₂CCl₃ | Barnyardgrass | 30 | 30 | 0 | 0 | 0 | NT |
| | | Crabgrass | 85 | 75 | 70 | 30 | 0 | NT |
| | | Foxtail | 30 | 10 | 0 | 0 | 0 | NT |
| | | Johnsongrass | 20 | 60 | 40 | 15 | 15 | NT |
| | | Wild Oats | 10 | 0 | 0 | 0 | 0 | NT |
| 2,6-diCl | 4-CH₂—C(O)—CH₂CCl₃ | Barnyardgrass | 85 | 85 | 85 | 80 | 60 | 60 |
| | | Crabgrass | 85 | 80 | 80 | 80 | 80 | 60 |
| | | Foxtail | 90 | 80 | 80 | 80 | 80 | 60 |
| | | Johnsongrass | 90 | 95 | 70 | 50 | 0 | 0 |
| | | Wild Oats | 80 | 80 | 70 | 60 | 40 | 10 |

NT = Not Tested

EXAMPLE 12

In a further illustrative representative operation, an aqueous composition containing 2,6-dichloro-4-(2-(2,2,2-trichloroethyl)oxiranyl)pyridine was prepared by mixing four parts by weight of the compound, 0.08 part by weight of sorbitan trioleate, and 0.02 part of a sorbitan monooleate polyoxyethylene derivative in about 40 ml of acetone. A portion of this concentrate composition was separately dispersed in a portion of water to provide an aqueous composition containing about 0.44 pound of the active ingredient per 100 gallons (0.5 g/liter) of ultimate treating composition.

The composition was applied to seedbeds previously seeded with cotton and yellow foxtail and the treated seeds covered with a thin layer of soil. Application of the treating composition was made at a rate sufficient to provide about one pound per acre (1.12 kg/hectare) of the active test ingredient. Thereafter, the treated seedbeds as well as untreated control seedbeds were held under conditions conducive to growth for a period of about two weeks and then examined. In the treated seedbeds, it was found that there was a thriving stand of cotton seedlings; but no yellow foxtail seedlings were evident. In the control seedbeds, observation showed thriving stands of both cotton and yellow foxtail seedlings.

Similar selective results are obtained in the presence of corn and soybeans when such crops are seeded with nutsedge, pigweeds, crabgrass, Johnson grass and barnyard grass and other active ingredients of the present invention are applied at various application rates.

Some of the compounds of this case exist with optically active centers, i.e.

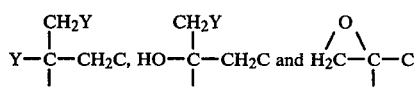

Enantiomorphs often show the same biological effect, but to a very different degree. A general discussion of this phenomenon may be found in A. Albert, *Selective Toxicity*, 4th Edition, Met Luen & Co., Ltd., London, 1968, pp. 387-390, and more particular discussions in A. Fredga and B. Åberg, "Stereoisomerism in plant growth regulators of the auxin type", *Ann. Rev. Plant Physiology* 16:53-72, 1965 and in E. J. Lien, J. F. R. DeMiranda and E. J. Ariens, "Quantitative structure-activity correlation of optical isomers", Molecular Pharmacology 12:598-604, 1976. The various enantiomers, mixtures and racemates of the above isomers are within the scope of the present invention.

We claim:

1. A substituted pyridyl compound having the formula

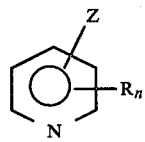

wherein Z is

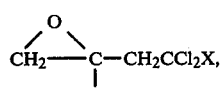

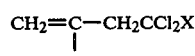

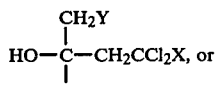

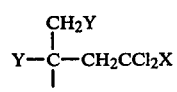

wherein X is hydrogen, chloro or methyl; Y is bromo or chloro; R is hydrogen, bromo, chloro, fluoro, $C_{1-4}$ alkyl, $C_{1-4}$ alkoxy, trifluoromethyl or nitro, and n is 1 or 2, with the proviso that at least one R substituent is other than hydrogen.

2. Compound of claim 1 which is 2,6-dichloro-4-(2-(2,2,2-trichloroethyl)oxiranyl)pyridine.

3. Compound of claim 1 which is 2-chloro-6-methoxy-4-(2-(2,2,2-trichloroethyl)oxiranyl)pyridine.

4. Compound of claim 1 which is 2-chloro-5-(3,3,3-trichloro-1-methylenepropyl)pyridine.

5. Compound of claim 1 which is α-(bromomethyl)-6-chloro-α-(2,2,2-trichloroethyl)-3-pyridine methanol.

6. Compound of claim 1 which is 2-chloro-5-(2-(2,2,2-trichloroethyl)oxiranyl)pyridine.

7. Compound of claim 1 which is chloro-6-(3,3,3-trichloro-1-methylenepropyl)pyridine.

8. Compound of claim 1 which is 2-trifluoromethyl-6-(2-(2,2,2-trichloroethyl)oxiranyl)pyridine.

9. Compound of claim 1 which is 2,6-dichloro-4-(3,3,3-trichloro-1-methylenepropyl)-pyridine.

10. Compound of claim 1 which is 2,5-dichloro-6-(2-(2,2,2-trichloroethyl)oxiranyl)pyridine.

11. Compound of claim 1 which is 2,3-dichloro-5-(2-(2,2,2-trichloroethyl)oxiranyl)pyridine.

12. Compound of claim 1 which is 2,4-dichloro-6-(2-(2,2,2-trichloroethyl)oxiranyl)pyridine.

13. Compound of claim 1 which is 2-chloro-6-(2-(2,2,2-trichloroethyl)oxiranyl)pyridine.

14. Compound of claim 1 which is 2,3-dichloro-5-(3,3,3-trichloro-1-methylenepropyl)pyridine.

15. Compound of claim 1 which is 2,5-dichloro-6-(3,3,3-trichloro-1-methylenepropyl)pyridine.

16. Compound of claim 1 which is 2,4-dichloro-6-(3,3,3-trichloro-1-methylenepropyl)pyridine.

17. Compound of claim 1 which is 5-(1-bromo-1-(bromomethyl)-3,3,3-trichloropropyl)-2-chloropyridine.

18. A herbicidal composition consisting essentially of an inert carrier and a herbicidally effective amount of a compound having the formula:

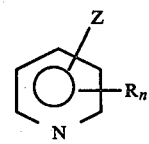

wherein Z is

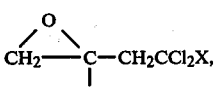

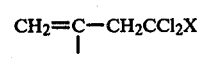

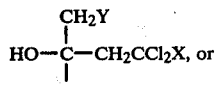

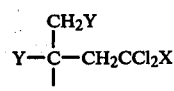

wherein X is hydrogen, chloro or methyl; Y is bromo or chloro; R is hydrogen, bromo, chloro, fluoro, $C_{1-4}$ alkyl, $C_{1-4}$ alkoxy, trifluoromethyl or nitro, and n is 1 or 2, with the proviso that at least one R substituent is other than hydrogen.

19. Composition of claim 18 wherein the compound is 2,6-dichloro-4-(2-(2,2,2-trichloroethyl)oxiranyl)pyridine.

20. Composition of claim 18 wherein the compound is 2-chloro-6-methoxy-4-(2-(2,2,2-trichloroethyl)oxiranyl)pyridine.

21. Composition of claim 18 wherein the compound is 2-chloro-5-(3,3,3-trichloro-1-methylenepropyl)pyridine.

22. Composition of claim 18 wherein the compound is α-(bromomethyl)-6-chloro-α-(2,2,2-trichloroethyl)-3-pyridine methanol.

23. Composition of claim 18 wherein the compound is 2-chloro-5-(2-(2,2,2-trichloroethyl)oxiranyl)pyridine.

24. Composition of claim 18 wherein the compound is 6-chloro-2-(3,3,3-trichloro-1-methylenepropyl)pyridine.

25. Composition of claim 18 wherein the compound is 2-trifluoromethyl-6-(2-(2,2,2-trichloroethyl)oxiranyl)-pyridine.

26. Composition of claim 18 wherein the compound is 2,6-dichloro-4-(3,3,3-trichloro-1-methylenepropyl)pyridine.

27. Composition of claim 18 wherein the compound is 3,6-dichloro-2-(2-(2,2,2-trichloroethyl)oxiranyl)pyridine.

28. Composition of claim 18 wherein the compound is 2,3-dichloro-5-(2-(2,2,2-trichloroethyl)oxiranyl)pyridine.

29. Composition of claim 18 wherein the compound is 2,4-dichloro-6-(2-(2,2,2-trichloroethyl)oxiranyl)pyridine.

30. Composition of claim 18 wherein the compound is 2-chloro-6-(2-(2,2,2-trichloroethyl)oxiranyl)pyridine.

31. Composition of claim 18 wherein the compound is 2,3-dichloro-5-(3,3,3-trichloro-1-methylenepropyl)pyridine.

32. Composition of claim 18 wherein the compound is 2,5-dichloro-6-(3,3,3-trichloro-1-methylenepropyl)pyridine.

33. Composition of claim 18 wherein the compound is 2,4-dichloro-6-(3,3,3-trichloro-1-methylenepropyl)pyridine.

34. Composition of claim 18 wherein the compound is 5-(1-bromo-1-(bromomethyl)-3,3,3-trichloropropyl)-2-chloropyridine.

35. A method for controlling undesired plant growth which consists essentially of applying a herbicidally effective amount of a compound having the formula:

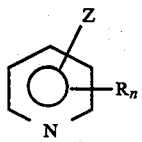
(I)

wherein Z is

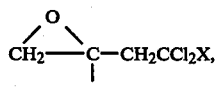

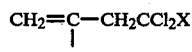

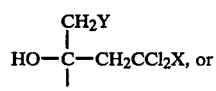

-continued $$\begin{array}{c} CH_2Y \\ | \\ Y-C-CH_2CCl_2X \\ | \end{array}$$

wherein X is hydrogen, chloro or methyl; Y is bromo or chloro; R is hydrogen, bromo, chloro, fluoro, $C_{1-4}$ alkyl, $C_{1-4}$ alkoxy, trifluoromethyl or nitro, and n is 1 or 2, with the proviso that at least one R substituent is other than hydrogen, to the locus of the undesired plants.

36. Method of claim 35 wherein the compound is 2,6-dichloro-4-(2-(2,2,2-trichloroethyl)oxiranyl)pyridine.

37. Method of claim 35 wherein the compound is 2-chloro-6-methoxy-4-(2-(2,2,2-trichloroethyl)oxiranyl)pyridine.

38. Method of claim 35 wherein the compound is 2-chloro-5-(3,3,3-trichloro-1-methylenepropyl)pyridine.

39. Method of claim 35 wherein the compound is α-(bromomethyl)-6-chloro-α-(2,2,2-trichloroethyl)-3-pyridine methanol.

40. Method of claim 35 wherein the compound is 2-chloro-5-(2-(2,2,2-trichloroethyl)oxiranyl)pyridine.

41. Method of claim 35 wherein the compound is 6-chloro-2-(3,3,3-trichloro-1-methylenepropyl)pyridine.

42. Method of claim 35 wherein the compound is 2-trifluoromethyl-6-(2-(2,2,2-trichloroethyl)oxiranyl)pyridine.

43. Method of claim 35 wherein the compound is 2,6-dichloro-4-(3,3,3-trichloro-1-methylenepropyl)pyridine.

44. Method of claim 35 wherein the compound is 2,6-dichloro-4-(2-(2,2,2-trichloroethyl)oxiranyl)pyridine.

45. Method of claim 35 wherein the compound is 2,3-dichloro-5-(2-(2,2,2-trichloroethyl)oxiranyl)pyridine.

46. Method of claim 35 wherein the compound is 2,4-dichloro-6-(2-(2,2,2-trichloroethyl)oxiranyl)pyridine.

47. Method of claim 18 wherein the compound is 2-chloro-6-(2-(2,2,2-trichloroethyl)oxiranyl)pyridine.

48. Method of claim 35 wherein the compound is 2,3-dichloro-5-(3,3,3-trichloro-1-methylenepropyl)pyridine.

49. Method of claim 35 wherein the compound is 2,5-dichloro-6-(3,3,3-trichloro-1-methylenepropyl)pyridine.

50. Method of claim 35 wherein the compound is 2,4-dichloro-6-(3,3,3-trichloro-1-methylenepropyl)pyridine.

51. Method of claim 35 wherein the compound is 5-(1-bromo-1-(bromomethyl)-3,3,3-trichloropropyl)-2-chloropyridine.

* * * * *